US007931673B2

(12) United States Patent
Hestad et al.

(10) Patent No.: US 7,931,673 B2
(45) Date of Patent: Apr. 26, 2011

(54) MINIMALLY INVASIVE VERTEBRAL ANCHOR ACCESS SYSTEM AND ASSOCIATED METHOD (75) Inventors: Hugh D. Hestad, Edina, MN (US); W. Matthew Kuester, St. Louis Park, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 949 days.

(21) Appl. No.: 11/567,238

(22) Filed: Dec. 6, 2006

(65) Prior Publication Data
US 2008/0140120 A1 Jun. 12, 2008

(51) Int. Cl.
*A61B 17/70* (2006.01)
(52) U.S. Cl. .................................. 606/246; 606/264
(58) Field of Classification Search .................. 606/104, 606/246, 300–321, 264–279, 60, 86 A, 96, 606/99
See application file for complete search history.

(56) References Cited

U.S. PATENT DOCUMENTS

| | | | |
|---|---|---|---|
| 5,242,443 A | 9/1993 | Kambin | |
| 6,235,028 B1 | 5/2001 | Brumfield et al. | |
| 6,951,538 B2 | 10/2005 | Ritland | |
| 7,008,424 B2 | 3/2006 | Teitelbaum | |
| 7,250,052 B2 | 7/2007 | Landry et al. | |
| 2004/0039384 A1 | 2/2004 | Boehm, Jr. et al. | |
| 2004/0138662 A1 | 7/2004 | Landry et al. | |
| 2004/0143265 A1 | 7/2004 | Landry et al. | |
| 2004/0147937 A1* | 7/2004 | Dunbar et al. | 606/99 |
| 2004/0172022 A1 | 9/2004 | Landry et al. | |
| 2005/0065517 A1 | 3/2005 | Chin | |
| 2005/0131408 A1* | 6/2005 | Sicvol et al. | 606/61 |
| 2005/0131421 A1 | 6/2005 | Anderson et al. | |
| 2005/0192589 A1 | 9/2005 | Raymond et al. | |
| 2005/0215999 A1 | 9/2005 | Birkmeyer et al. | |
| 2005/0228380 A1 | 10/2005 | Moore et al. | |
| 2005/0234449 A1 | 10/2005 | Aferzon | |
| 2006/0036255 A1 | 2/2006 | Pond, Jr. et al. | |
| 2008/0125788 A1* | 5/2008 | Cohen et al. | 606/104 |

FOREIGN PATENT DOCUMENTS

| | | |
|---|---|---|
| FR | 2697991 A1 | 5/1994 |
| WO | 2004041100 A1 | 5/2004 |
| WO | 2006067837 A1 | 6/2006 |

OTHER PUBLICATIONS

Zimmer Spine, Silhouette Spinal Fixation System, Catalog, Mar. 2005, 6 pgs.

* cited by examiner

*Primary Examiner* — Eduardo C Robert
*Assistant Examiner* — Christina Negrelli
(74) *Attorney, Agent, or Firm* — Seager, Tufte & Wickhem, LLC (57) ABSTRACT

A spinal fixation access system includes a vertebral anchor with selectively attached extension members to extend percutaneously from the spine. The surgical procedure associated with this invention involves making small, discrete incisions for the placement of select vertebral anchors. The extension members retract soft tissue, muscle and the like to thereby provide visibility and access to the head of the anchor. Through the extension members, instrumentation such as a spine rod, set screw and other required hardware may be delivered to the anchors. Once a spine rod or other components are secured to the pedicle screws, the extension members are disengaged from the anchors and removed from the patient.

22 Claims, 10 Drawing Sheets

MINIMALLY INVASIVE VERTEBRAL ANCHOR ACCESS SYSTEM AND ASSOCIATED METHOD

BACKGROUND

This invention relates generally to spinal fixation devices and more specifically relates to a system and associated method for minimally invasive installation of vertebral anchors and connecting elements of spinal fixation constructs.

The human spinal column is a highly complex system of bones and connected tissues that provide support for the body and protects the delicate spinal cord and nerves. The spinal column includes a series of vertebrae stacked one atop the other. Each vertebral body includes a relatively strong cortical bone portion forming the outside surface of the body and a relatively weak cancellous bone portion forming the center of the body. An inter-vertebral disc is situated between each vertebral body that provides for cushioning and dampening of compressive forces applied to the spinal column. The vertebral canal containing delicate spinal cords and nerves is located just posterior to the vertebral bodies.

A variety of types of spinal column disorders may be caused by abnormalities, disease, trauma or the like and result in debilitating pain as well as diminished nerve function in many cases. One known technique to address many such spinal conditions is commonly referred to as spinal fixation. Surgical implants are used for fusing together and/or mechanically immobilizing adjacent vertebrae of the spine. Spinal fixation may also be used to improve the position of the adjacent vertebrae relative to one another so as to alter the overall alignment of the spine. Such techniques have been used effectively to treat many spinal conditions and to relieve pain suffered by the patient.

One particular spinal fixation technique includes immobilizing the spine by using orthopedic spine rods which run generally parallel to the spine. This is accomplished by exposing the spine posteriorly and fastening hooks or bone screws to the pedicles of the appropriate vertebrae. The vertebral anchors or screws are generally placed two per vertebrae, one at each pedicle on either side of the spinal column and serve as anchor points for the spine rods. The aligning influence of the rods forces the spine to conform to a more desirable shape. In many cases, the spine rods are bent to achieve the desired curvature of the spinal column.

Installation of such spinal fixation constructs conventionally requires a surgeon to prepare a long incision aligned with the spinal column of a patient. The pedicle screws, hooks or other vertebral anchors are then attached to a number of vertebrae after which the spine rod is located with respect to saddles or U-shaped channels attached to the vertebral anchors. The spine rod is then bent to match the relative position of the anchor heads. Visualization of the accuracy of the alignment of the spine rod and the anchor heads may be difficult because of visual interference from tissue and blood in the surgical field. Conventional surgical methods require a large midline incision and retraction of skin, muscle and other tissue to provide the surgeon with sufficient visualization of the pedicle bone structure.

The accuracy of the placement and configuration of the spine fixation elements are very important. In combination with the relatively long incision required for the installation of the fixation construct, extended surgical procedures and related difficulties or complications are generally recognized as major contributing influences for extended patient recovery and less than optimal spinal fixation results.

SUMMARY OF THE INVENTION

This invention addresses these and other shortcomings in the prior art. The devices and methods associated with this invention are used to aid in the surgery for vertebral stabilization using pedicle hooks, screws, anchors and fixation components.

According to various embodiments of this invention, vertebral anchors such as pedicle screws are inserted into the target vertebrae of a patient's spinal column. The pedicle screw may be cannulated for proper positioning and installation. In one aspect, this invention provides an access system which involves a pedicle screw with an extension member adapted to be coupled to the anchor and extend percutaneously from the spine. The surgical procedure associated with this invention involves making small, discrete incisions for the placement of select pedicle screws. The extension members on the pedicle screws retract soft tissue, muscle and the like to thereby provide the surgeon visibility and access to the head of the pedicle screw. Through the extension member, instrumentation such as a spine rod, set screw and other required hardware may be delivered to the pedicle screws.

In another aspect of this invention, a deformation arrangement is used to couple the extension member to the anchor head. In one embodiment, the deformation arrangement is a flange on one end of the extension member and one or more slits in the flange allow the flange to expand when being installed and removed from the anchor head.

Once the extension member is secured on the anchor, a restrictor is coupled to the flange to inhibit expansion of the deformation arrangement and maintain secure placement of the extension member on the anchor while the spinal fixation construct is being installed or serviced. The extension members for each pedicle screw extend beyond the surface of the skin (i.e., percutaneously) thereby retracting soft tissue and muscle enabling the surgeon to install the spinal fixation construct with smaller discrete incisions as opposed to an extended incision. As such, a more minimally invasive surgical procedure can be accomplished with this invention thereby allowing for visualization of the installation components during the surgery and promoting patient recovery post-surgery.

As a result of these and other aspects of this invention, increased efficiency and accuracy is provided for installation of a spinal fixation construct in a minimally invasive atmosphere thereby promoting patient recovery and optimum spinal surgery results.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION OF THE INVENTION

Figure 1:
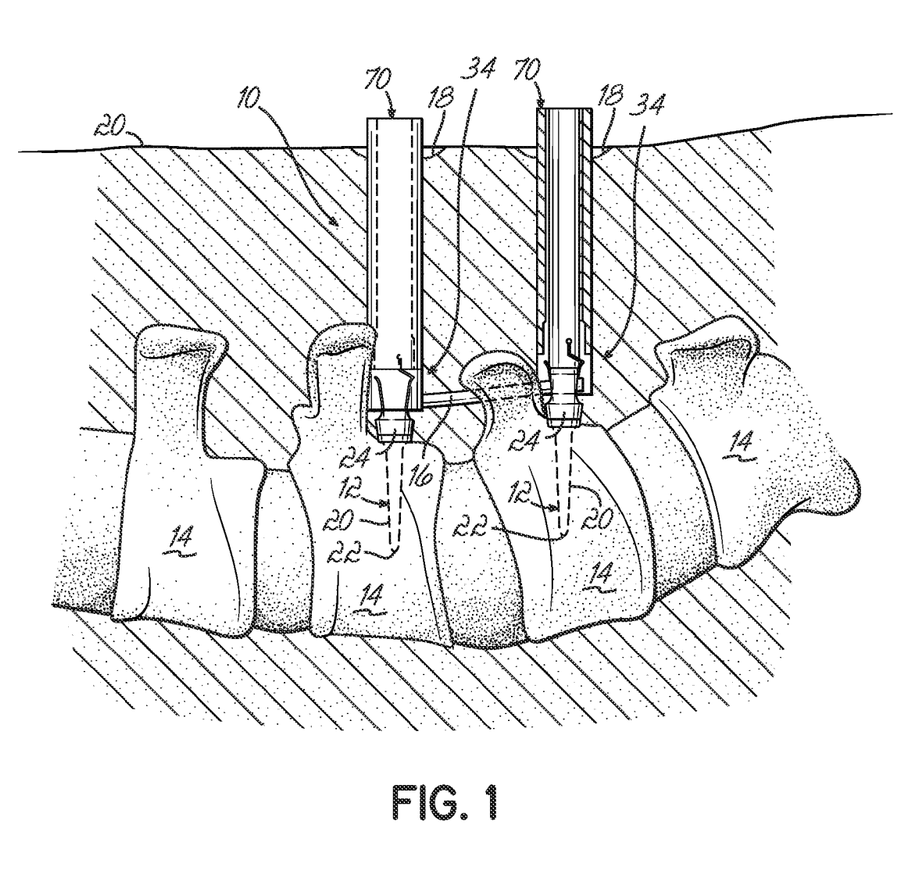
FIG. 1 is a side elevational and partial cross-sectional view of a spinal fixation construct being surgically implanted in selected vertebrae of a patient's spine according to one embodiment of this invention.

Referring to the Figs., various embodiments of a minimally invasive spinal fixation construct 10 and associated installation method are shown. In FIG. 1, the spinal fixation construct 10 includes a number of vertebral anchors 12 which in one embodiment are each pedicle screw assemblies, each of which is inserted into selected vertebrae 14 of a patient. The pedicle screw assemblies 12 are joined together in the spinal fixation construct by a connecting element 16 which in one embodiment is a spine rod. The connecting element 16 may be something other than a rigid rod according to alternative embodiments of this invention. According to various aspects of this invention, the individual pedicle screw assemblies 12 may be inserted into the patient through discrete and often individual incisions 18 in the patient's skin 20. In certain instances, a single incision 18 may be available to provide installation of multiple pedicle screw assemblies 12 in adjacent vertebrae 14. The small, discrete incisions 18 provide the opportunity for insertion of a cannulated pedicle screw via a K-wire (not shown) inserted through the incision 18 to the precise location on the vertebrae 14 for proper installation of the pedicle screw 12. While cannulated and other pedicle screw assemblies are shown and described herein, one of ordinary skill in the art will appreciate that other types of vertebral anchors and vertebrae engaging mechanisms can be utilized such as hooks for anchoring the connecting element 16 to the patient's spinal column.

As shown generally in FIGS. 1 and 5-8, a vertebral anchor 12 according to one embodiment of this invention includes a pedicle screw 12 having a threaded shaft 20 and a distal tip 22 for insertion and stable positioning into the pedicle area of the patient's vertebrae 14. The pedicle screw 12 shown herein is a polyaxial pedicle screw in which a polyaxial body 24 mounted opposite from the distal tip 22 of the screw 12 to a screw head 26 provides for a variety of orientations of the polyaxial body 24 relative to longitudinal axis of the screw 12 as is common with many pedicle screw systems. The polyaxial body 24 coupled to the pedicle screw head 26 includes a saddle or U-shaped channel 28 (FIGS. 19-20) formed between a pair of spaced arms 30 extending upwardly. The polyaxial body 24 is adapted to receive the spine rod 16 in the saddle or U-shaped channel 28 and the spine rod 16 is securely retained by the polyaxial body 24 via a fastener such as a set screw 32 (FIG. 8) threadably received therein as is common with many known pedicle screw systems.

One aspect of various embodiments of this invention includes an extension member 34 projecting upwardly from the vertebral anchor head 24 as shown in FIGS. 1 and 5-8. Due to the relative position and configuration of the extension members 34 on the vertebral anchors 12 according to embodiments of this invention, slots 36 are provided and in communication with the U-shaped channel or saddle 28 of the anchor head 24. Advantageously, the extension members 34 project through the incision 18 such that a proximal end 38 of the members 34 is located percutaneously above the patient's skin when the anchor 12 is inserted into the vertebrae 14 as shown in FIG. 1.

Figure 2:
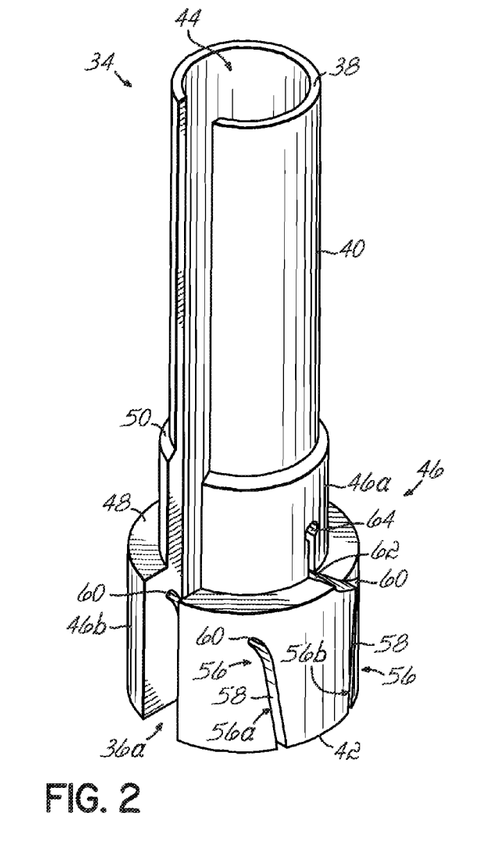
FIG. 2 is a perspective view of a vertebral anchor extension member utilized in the spinal fixation construct shown in FIG. 1.
Figure 3:
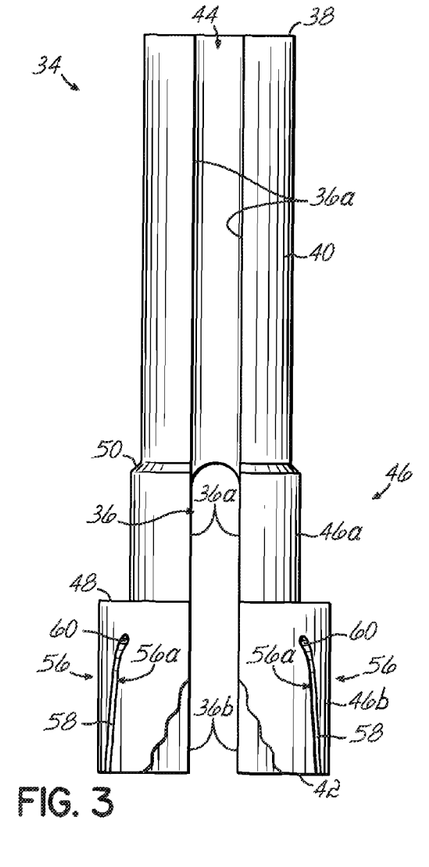
FIG. 3 is a front elevational view of the extension member of FIG. 2.

One embodiment of an extension member 34 according to this invention is shown particularly in FIGS. 1-8. The extension member 34 is elongate and adapted to extend percutaneously from the body when the anchor 12 is secured to the patient's vertebrae 14. The elongate extension member 34 in this embodiment is an elongate tubular sleeve having a generally arcuate sidewall 40 with a generally circular cross-sectional configuration. The extension member 34 has a first more distal end 42 adapted to be coupled to the anchor head 24 and the second or proximal end 38 adapted to be positioned percutaneously for access to the anchor head 24 through a lumen 44 formed by the arcuate sidewall 40 of the extension member 34. The first end 42 of the extension member 34 includes a flange 46 having an enlarged diameter relative to the sidewall 40 of the extension member 34. As shown most clearly in FIGS. 2-4, the flange 46 has an upper and a lower portion 46a, 46b with a shoulder 48 formed in between them. A beveled rim 50 forms a transition from the flange 46 to the sidewall 40 of the extension member 34. As shown in FIGS. 2 and 3, the extension member 34 includes a full-length slot 36a and a distal slot 36b positioned diametrically opposite from the full-length slot 36a. Both of the slots 36a, 36b are in communication with the distal end 42 of the extension member 34.

Figure 5:
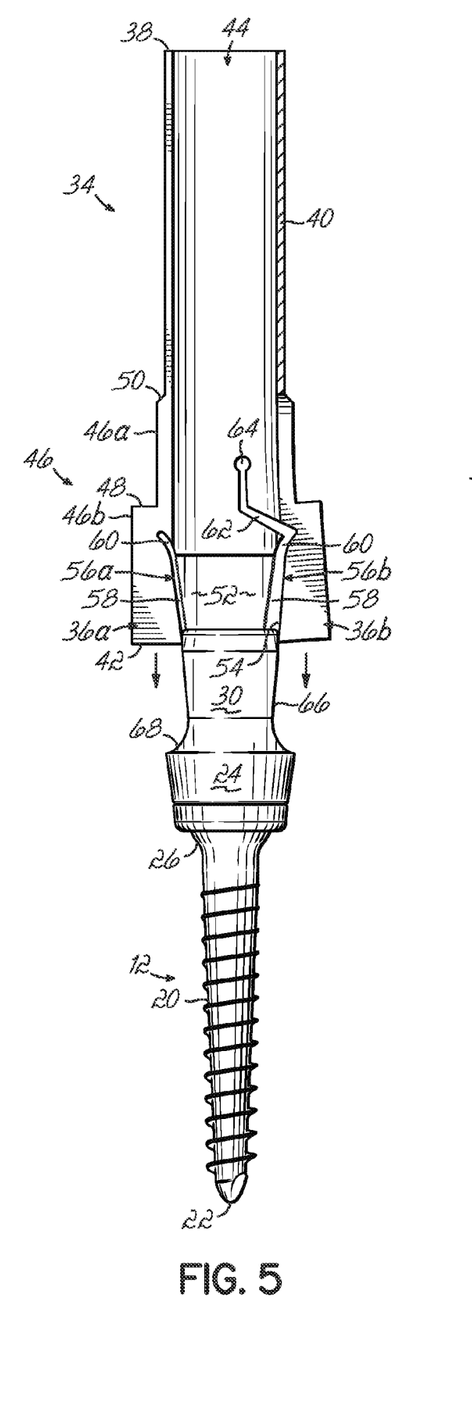
FIG. 5 is a side elevational view of the extension member of FIG. 2 being coupled to a vertebral anchor in the form of a pedicle screw.
Figure 6:
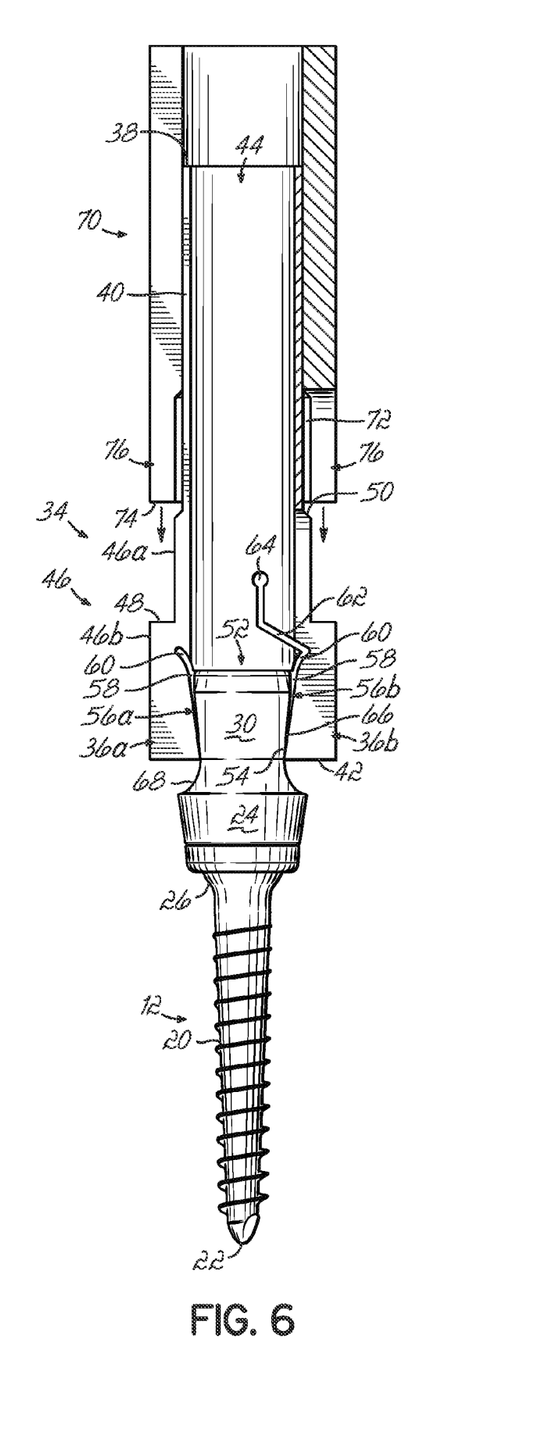
FIG. 6 is a view similar to FIG. 5 with a restrictor being installed on the extension member.

Referring particularly to FIGS. 5 and 6, a socket 52 is formed on the interior of the flange 46 and is sized and configured to meet with the anchor head 24 when the extension member 34 is mounted to the anchor 12. In this embodiment of the invention, the socket 52 has a generally upwardly tapered configuration with a throat or entry region 54 being more narrow than the upper portion of the socket 52. This contour corresponds to the contour of the anchor head 24 thereby providing a snug and secure mating relationship as shown generally in FIG. 6.

Figure 4:
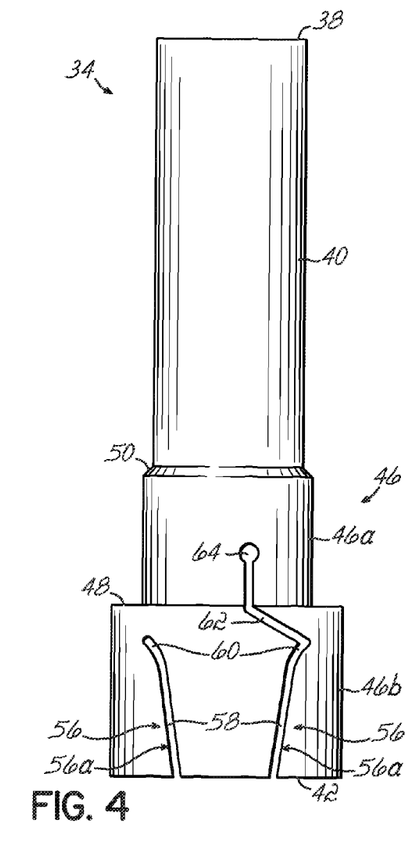
FIG. 4 is a side elevational view of the extension member of FIG. 2.

One aspect of the extension member 34 according to this embodiment of the invention is one or more slits 56 in the flange 46 which allow the flange 46 to temporarily expand or deform while the extension member 34 is being coupled to or uncoupled from the anchor 12. As shown most clearly in FIGS. 2-4, the flange 46 includes a number of minor slits 56a which have a main portion 58 angled relative to the longitudinal axis of the extension member 34 and terminate in the lower portion 46b of the flange with a hook 60. One or more major slits 56b are also provided in the flange 46 and the major slits include a main portion 58 similar to the configuration of the minor slits. The major slits each also include an adjoining hook portion 60. The minor slits 56a terminate with the hook portion 60 whereas the major slits 56b include an angled portion 62 projecting from the hook portion 60. The angled portion 62 transitions the major slit 56b through the shoulder 48 of the flange 46. The major slit 56b terminates in a keyhole-shaped configuration 64 which is aligned generally with the longitudinal axis of the extension member 34 (FIG. 4). In alternative embodiments, any number and/or configuration of sized or shaped slits can be used to provide for the desired deflection characteristics.

The major and minor slits 56ab, 56a allow the flange 46 of the extension member 34 to temporarily expand as the throat 54 of the extension member 34 passes over the outwardly tapered proximal portion 66 of the anchor head 24. Continued downward movement of the extension member 34 as shown in FIG. 5 allows the larger diameter proximal portion 66 of the anchor head 24 to enter into the larger diameter portion of the socket 52 in the flange 46 and the reduced neck region 68 of the anchor head 24 seats within the reduced diameter throat 54 of the flange 46. The slits 56 allow the flange 46 to expand outwardly as shown in FIG. 5 until the anchor head 24 is seated within the socket 52 as shown in FIG. 6. At that time, the slits 56 allow the flange 46 on the extension member 34 to relax into a mating configuration with the anchor head 24.

While the portion 66 of the anchor head 24 and the socket 52 are shown and described as having tapered, mating configuration, other configurations and designs are envisioned within the scope of this invention to provide a retained fit between the extension member 34 and the anchor head 24.

Figure 7:
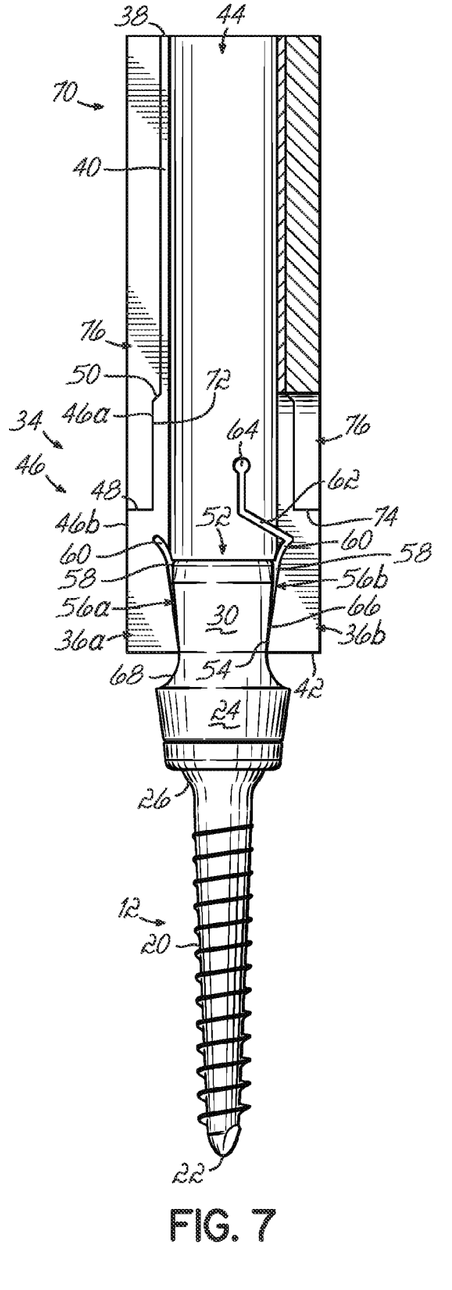
FIG. 7 is a view of the assembled vertebral anchor and extension member according to the first embodiment of this invention.

Another aspect of this embodiment of the invention is a restrictor 70 which when selectively coupled to the extension member 34 inhibits deformation of the flange 46. In one embodiment, the restrictor 70 is an elongate collar which telescopically fits downwardly around the sidewall 40 of the extension member 34. As shown in FIG. 6, the collar or restrictor 70 includes an internal cavity 72 sized and configured to mate with the upper portion of the flange 46a and the lowermost edge 74 of the collar seats upon the shoulder 48 of the flange 46 as shown in FIG. 7. With the collar 70 mated onto the extension member 34, expansion of the flange 46 is restricted thereby adding to the secure mating relationship of the extension member 34 on the anchor 12. The collar 70 inhibits the flange 46 from expanding and restricts the slits 56 from expanding. The upper end of the collar 70 may extend percutaneously through the incision 18 as shown in FIG. 1. The collars 70 may include slots 76 corresponding to the orientation, size and configuration of the slots 36 in the extension members 34. When the collars 70 are telescopically mated with the extension members 34, the slots 36, 76 in the respective components are aligned.

Referring to FIGS. 9-21, a second embodiment of this invention is shown. This embodiment of the invention also includes an extension member 34 adapted to be coupled to the head 24 of the anchor 12 to provide access for the surgeon during installation of the spinal fixation construct 10. The extension member 34 of this embodiment also utilizes a restrictor 70 to inhibit expansion or deformation of the flange 46 on the extension member 34 coupled to the anchor head 12.

Figure 9:
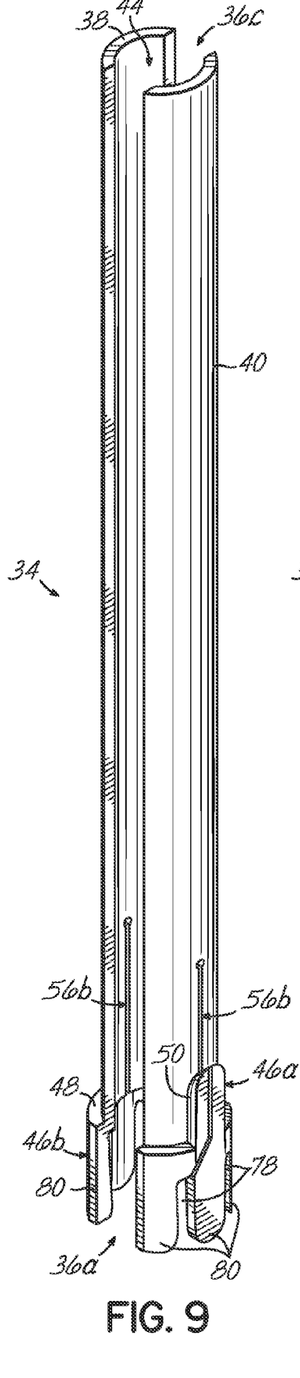
FIG. 9 is a perspective view of a second embodiment of a vertebral anchor extension member utilized in a spinal fixation construct according to this invention.
Figure 10:
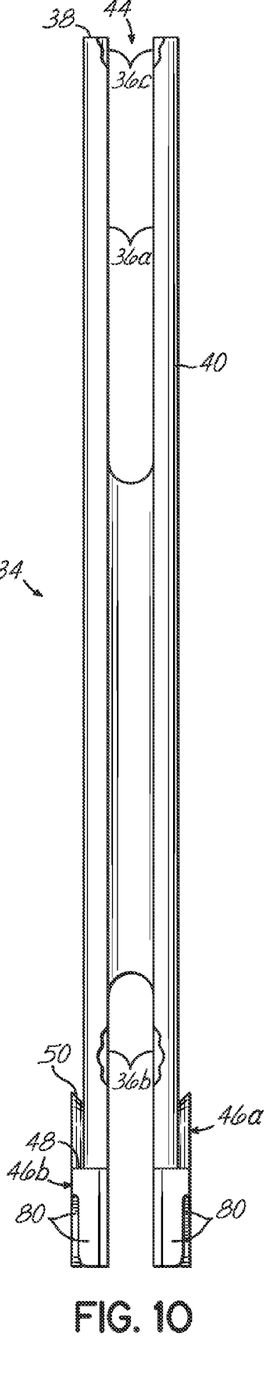
FIG. 10 is a front elevational view of the extension member of FIG. 9.
Figure 11:
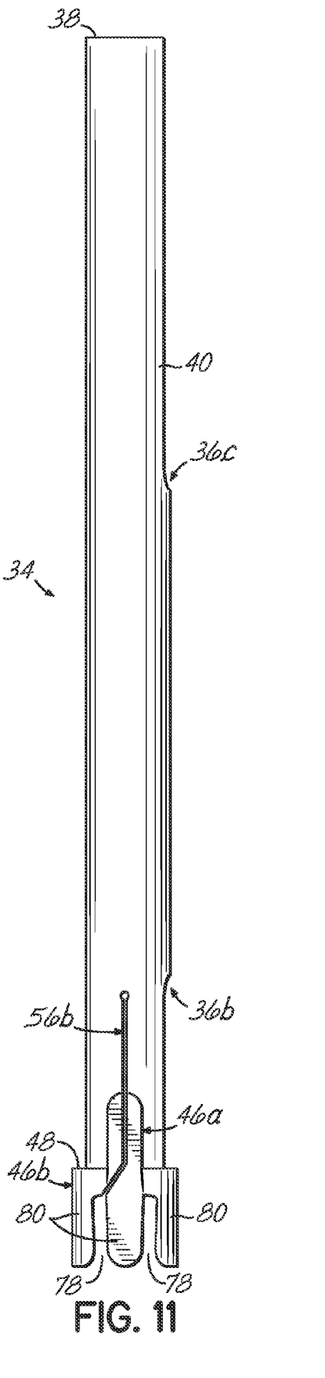
FIG. 11 is a side elevational view of the extension member of FIG. 9.

As shown in FIGS. 9-11, the extension member 34 includes the full-length slot 36a and two partial-length slots 36b, 36c each extending from opposite ends of the extension member 34 (FIG. 10). Moreover, the flange 46 according to this embodiment of the extension member includes the lower portion 46b and shoulder 48. However, the upper portion of the flange 46a does not extend around the entire circumference of the sidewall 40 and is formed in two diametrically opposite sections 46a, 46a which extend upwardly from the shoulder 48. A major slit 56b extends through each of the upper flange portions 46a as shown in FIGS. 9 and 11. Moreover, notches 78 are provided in the flange 46 to separate the flange 46 into downwardly projecting lugs 80 formed between the notches 78. The major slit 56b originates in one of the notches 78 and projects through the upper portion of the flange 46a and into the sidewall 40 of the extension member 34 as shown in FIGS. 9 and 11. The peripheral rim 50 of the upper portion of the flange 46a is undercut as shown most clearly in FIG. 10. The undercut rim 50 of the upper flange portion 46a extends around the entire perimeter of that component.

Figures 12, 13:
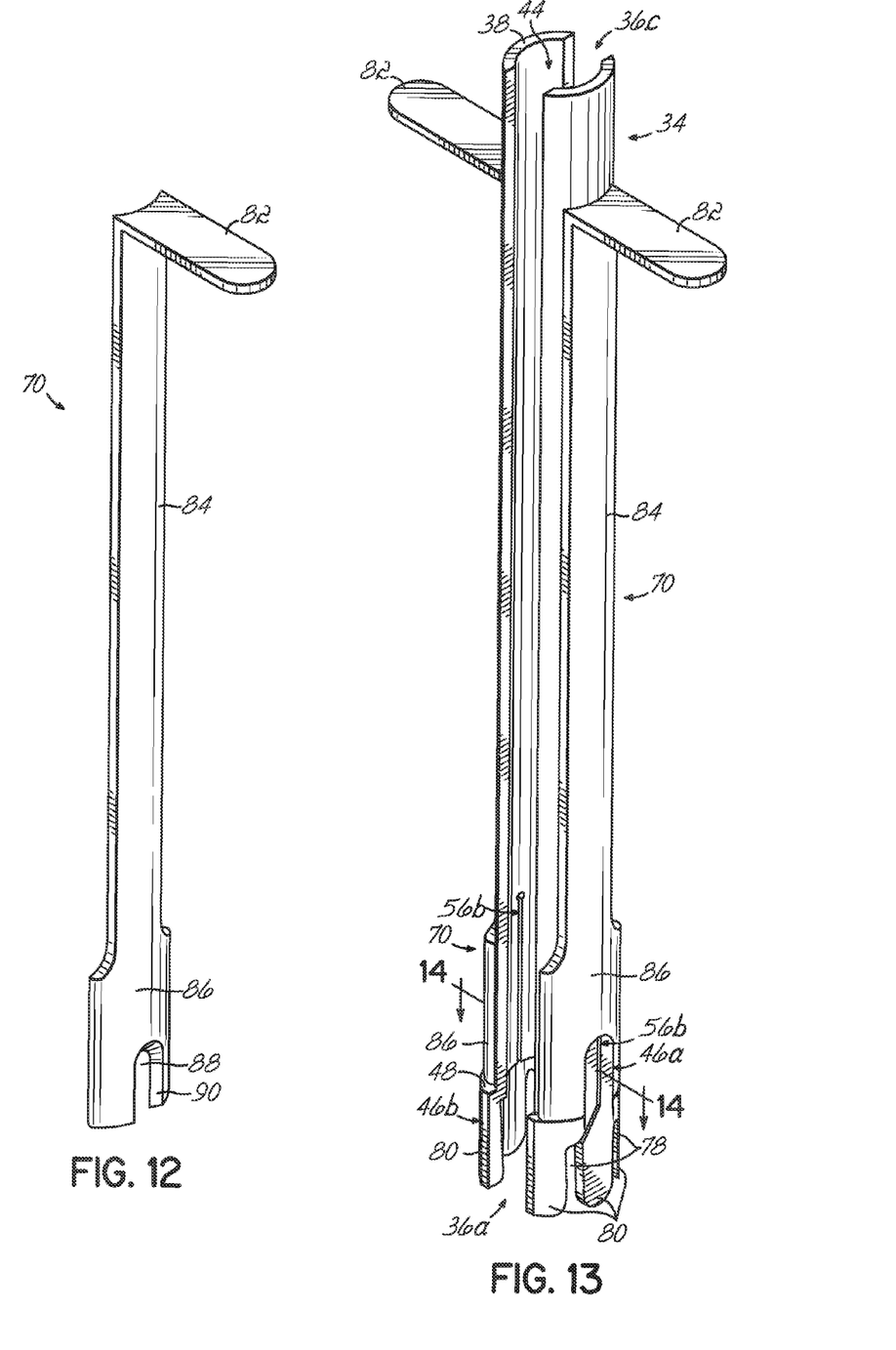
FIG. 12 is a perspective view of a restrictor according to one embodiment for use with the extension member of FIG. 9.
FIG. 13 is a perspective view of a pair of restrictors as shown in FIG. 12 assembled with the extension member of FIG. 9.
Figures 14, 15:
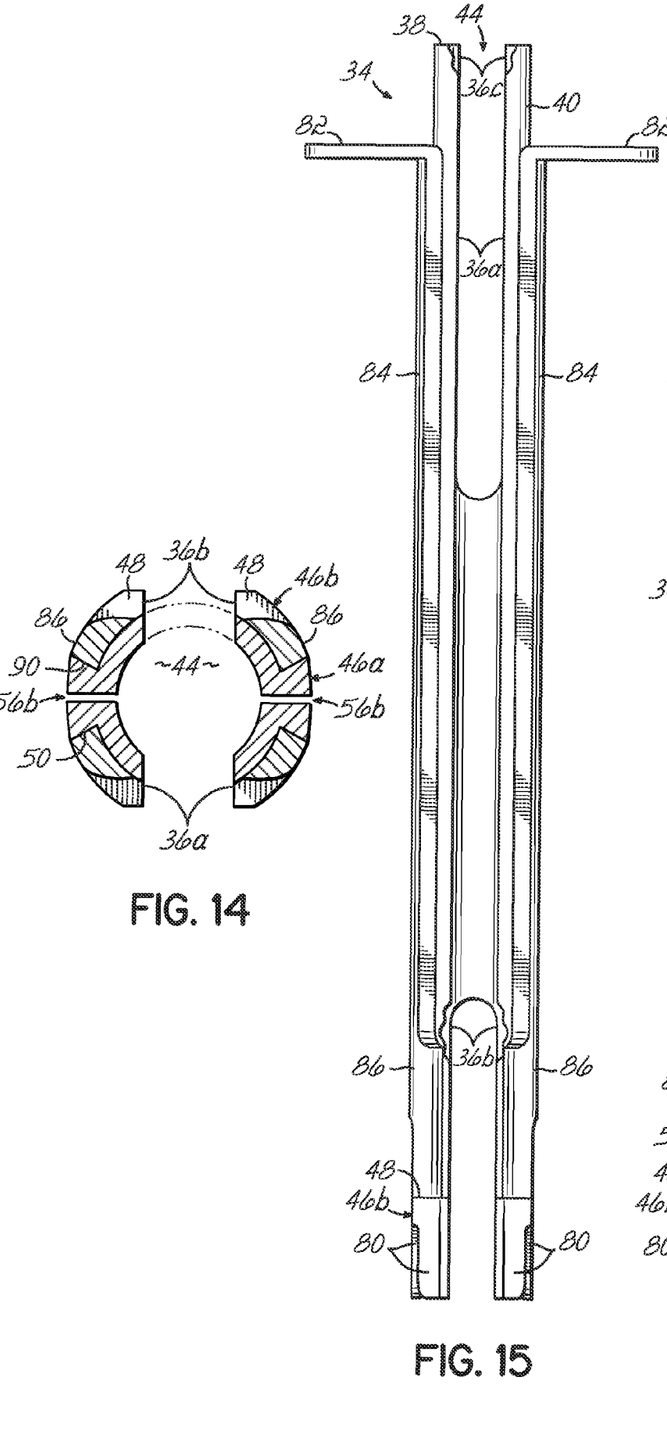
FIG. 14 is a cross-sectional view taken along line 14-14 of FIG. 13.
FIG. 15 is a front elevational view of the embodiment of FIG. 13 with the extension member assembled with a restrictor.
Figure 16:
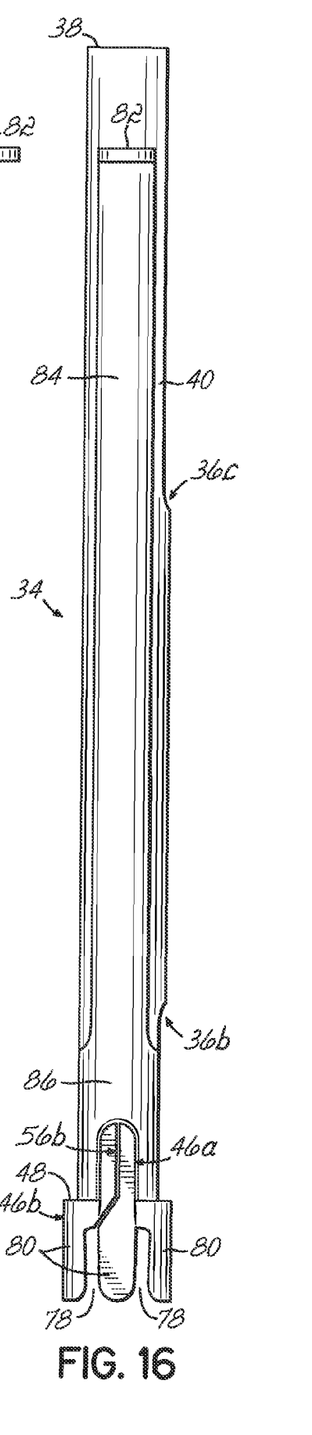
FIG. 16 is a side elevational view of the assembly of FIG. 15.
Figure 17:
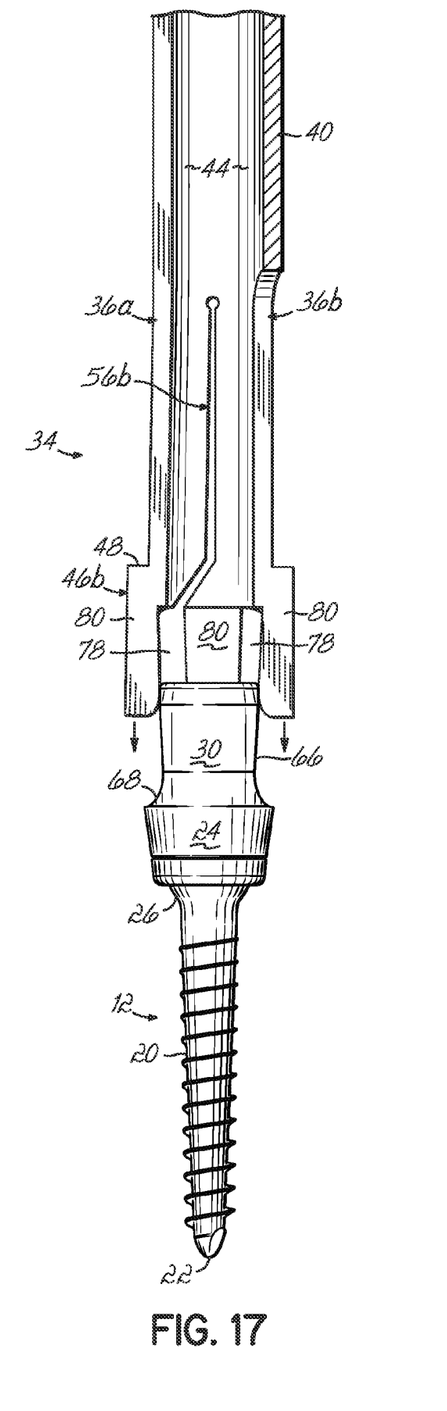
FIG. 17 is a side elevational view in partial cross-section of the extension member of FIG. 15 being coupled to a vertebral anchor in the form of a pedicle screw.
Figure 18:
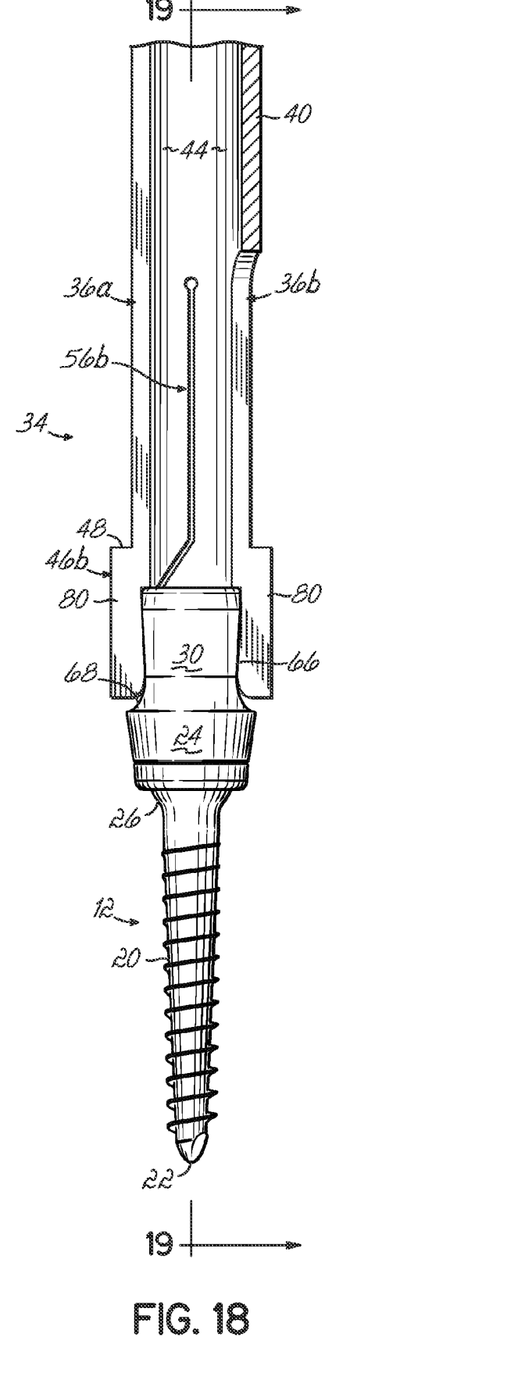
FIG. 18 is a view similar to FIG. 17 with the extension member mounted on the pedicle screw.
Figure 19:
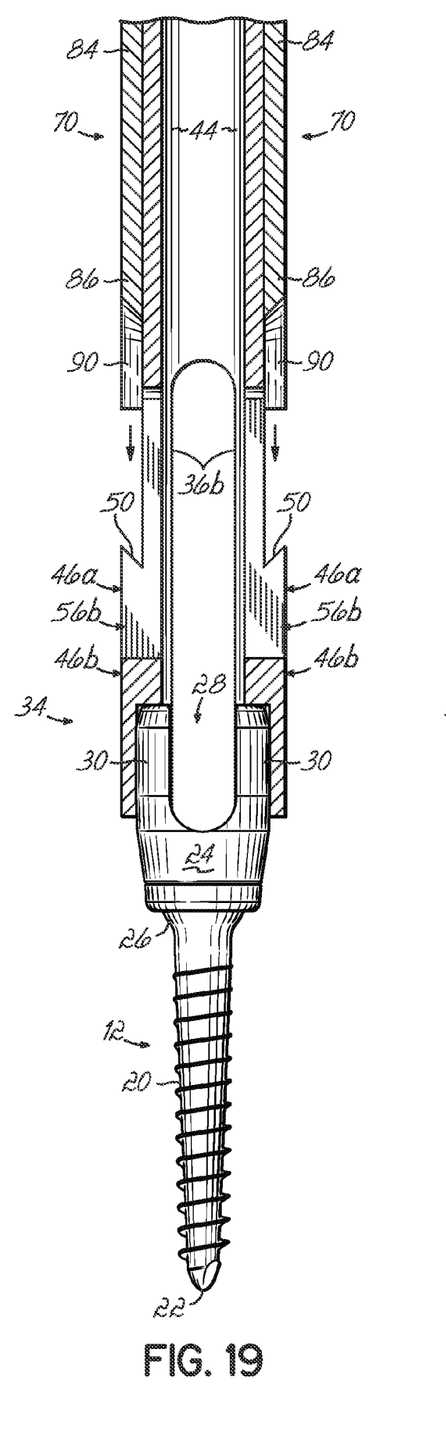
FIG. 19 is a cross-sectional view taken along line 19-19 of FIG. 18 of a restrictor being installed on the extension member.
Figure 20:
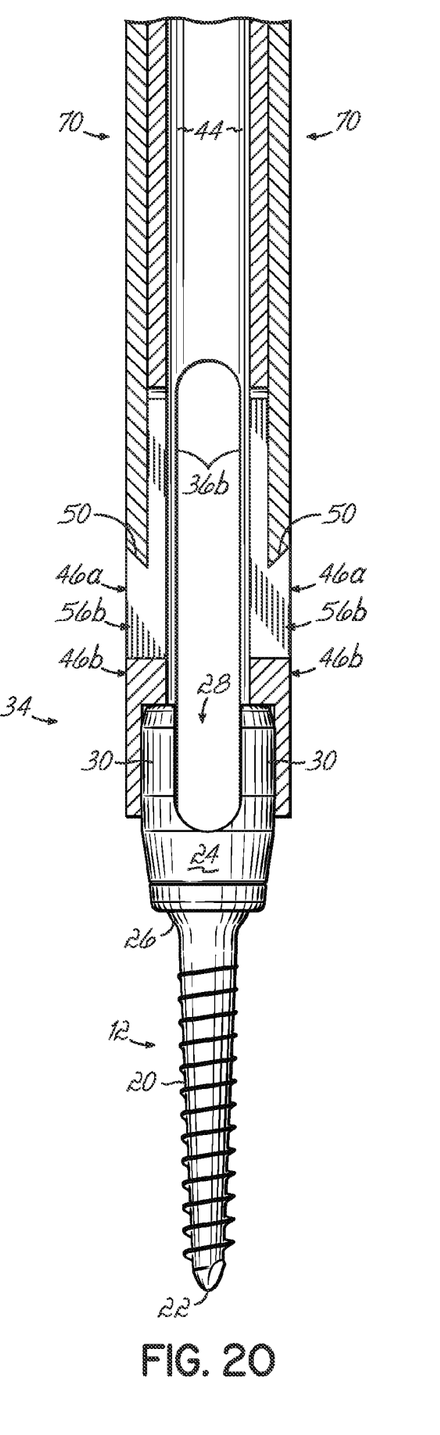
FIG. 20 is a view of the assembled vertebral anchor and extension member of FIG. 19.

The restrictor 70 according to this embodiment of the invention is shown particularly in FIGS. 12 and 13. The restrictor 70 is provided in two distinct members, one identical with the other. The restrictor 70 has a generally L-shaped configuration with an upper tab 82 projecting generally perpendicular from the major body portion 84 of the restrictor 70. The restrictor 70 has a lower enlarged yoke portion 86 at an opposite end from the tab 82. The yoke portion 86 includes a U-shaped recess 88 providing a bifurcated configuration to the yoke 86. The U-shaped recess 88 is bounded by a sloped edge go which is sized and configured to mate with the tapered rim 50 of the upper portion of the flange 46a to form a dove tail or rabbet joint as shown in FIGS. 13-16. A pair of the restrictors 70 on diametrically opposite sides of the extension member 34 and are each aligned with the one of the upper flanges 46a, 46a and inserted downwardly as shown in FIG. 19 until the U-shaped recess 88 of each restrictor 70 is seated on the associated upper flange portion 46a of the extension member 34. The configurations of the rim of the upper flange 46b and the U-shaped recess edge go provide positive locking engagement in the form of a rabbet or miter joint (FIG. 14) to thereby inhibit expansion of the extension member 34 after it is seated upon the anchor head 24 as shown in FIG. 20. In alternative embodiments, the restrictors 70 may be modular relative to extension member 34 or integrated as a single functioning assembly or unit and may utilize a variety of mating geometries, not just a dovetail or rabbet joint.

Figure 21:
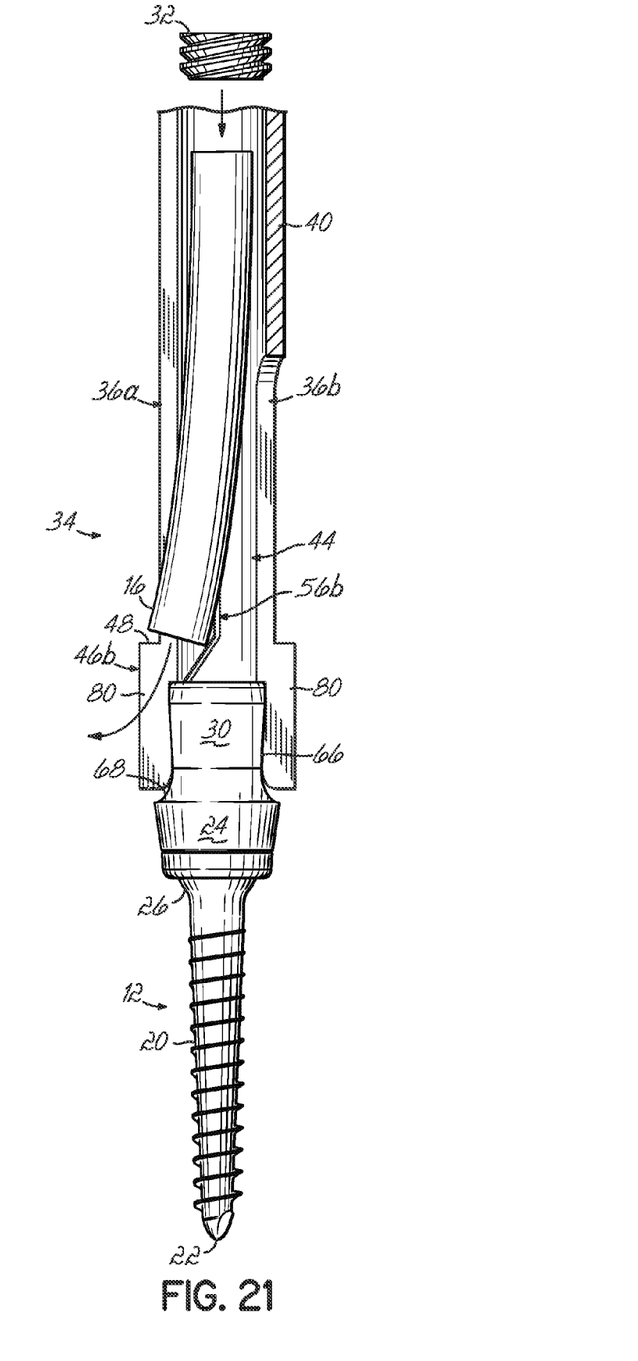
FIG. 21 is a partial cross-sectional view of the vertebral anchor and extension member of FIG. 20 with a spine rod and set screw being inserted through the extension member.

Similar to other previous described embodiments of this invention, once the extension member 34 and restrictors 70 are seated on the anchor head 24, the connecting member 16 in the form of a spine rod may be inserted through the lumen 44 formed in the extension member 34 toward the anchor head 24 for installation onto the vertebral anchors 12 on the spinal fixation construct 10. The set screw 32 may subsequently be inserted through the lumen 44 for mating with the anchor 12 as shown in FIG. 21.

Figure 8:
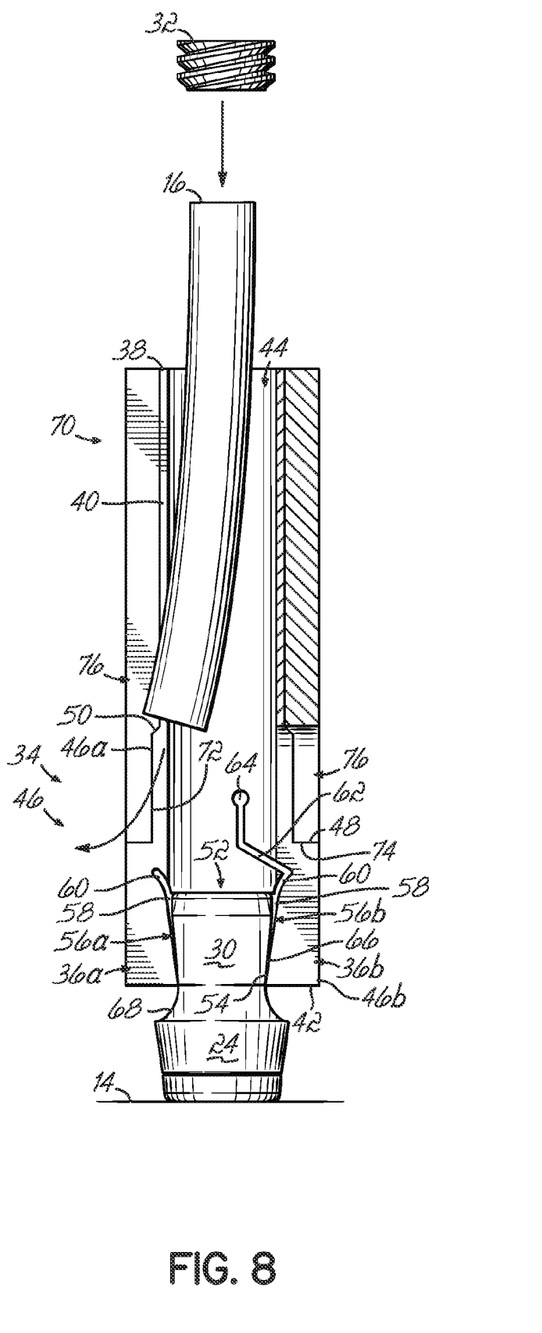
FIG. 8 is a partial cross-sectional view of the assembled vertebral anchor and extension member of FIG. 7 with a spine rod and set screw being inserted through the extension member.

One advantage provided by this invention is shown generally in FIG. 1. With the pedicle screws 12 inserted into the appropriate vertebrae 14, the extension members 34 project from the screw assemblies 12 percutaneously. The enhanced visualization and access afforded by the percutaneous positioning of the extension members 34 in the general orientation of the associated anchors 12 is a significant advantage for the accurate and precise positioning of the spinal fixation components. Referring to FIGS. 8 and 21, the spine rod 16 may be inserted through the slots and into the saddles 28 of the anchors 12. This may be accomplished with incisions 18 which are adjacent to the pedicle screw assemblies 12 as shown in FIG. 1. The access slots provided in the extension member 34 and the restrictors 70 provide communication between the various adjacent pedicle screw assemblies 12 so that the spine rod 16 may be inserted into the saddles 28 of the anchor heads 24 in a minimally invasive and less disruptive procedure than previously realized.

Once the set screws 32 are installed in the anchor heads 24, the restrictors 70 and then the extension members 34 can be removed from the anchors 12 and out of the patient through the incisions 18. The slits 56 allow for expansion of the flange 46 once the restrictor 70 is removed to permit the anchor head 24 removal from the socket 52.

As a result, a more minimally invasive spinal fixation construct installation procedure is provided by the pedicle screw assemblies, collars and associated devices of this invention without the need for extended incision and associated difficulties. Moreover, increased visualization and minimally invasive disruption are realized with this invention.

From the above disclosure of the general principles of this invention and the preceding detailed description of at least one embodiment, those skilled in the art will readily comprehend the various modifications to which this invention is susceptible. Therefore, we desire to be limited only by the scope of the following claims and equivalents thereof.

We claim:

1. A vertebral anchor system comprising:
   an anchor having a head and being adapted to be secured to a patient's vertebrae;
   an extension member adapted to be selectively coupled to the anchor head to provide access to the anchor when coupled thereto, the extension member having a tubular sidewall having a first slot adapted to provide access to regions of the spine adjacent to the anchor, the first slot extending substantially the full height of the extension member, the extension member having a second slot in the sidewall extending less than the full height of the extension member;
   a deformation arrangement on the extension member permitting a portion of the extension member to deform during installation and removal of the extension member on to and from, respectively, the anchor head, the deformation arrangement including one or more slits extending proximally from a distal end of the extension member, wherein the portion of the extension member is deformed by expanding or contracting at least one of the one or more slits; and
   a restrictor adapted to be selectively coupled to the extension member to inhibit deformation of the deformation arrangement when coupled thereto.

2. The anchor system of claim 1 wherein the anchor is a pedicle screw having a threaded shaft adapted to be inserted into a pedicle of the vertebrae and the anchor head is a polyaxial body adapted to be positioned in a plurality of orientations relative to a longitudinal axis of the threaded shaft.

3. The anchor system of claim 1 further comprising:
   a set screw adapted to threadably engage the anchor head and secure a connecting member relative to the anchor.

4. The anchor system of claim 1 wherein the extension member is elongate and adapted to extend percutaneously from the body when the anchor is secured to the patient's vertebrae.

5. The anchor system of claim 1 wherein the extension member is an elongate sleeve having a distal end adapted to be coupled to the anchor head and a proximal end spaced therefrom and adapted to be positioned percutaneously for access to the anchor head via the sleeve.

6. The anchor system of claim 1 further comprising:
   a flange on the distal end of the extension member; and
   a socket formed by the flange adapted to receive therein the anchor head; and
   two or more slits in the flange, the slits and flange combining to form the deformation arrangement.

7. The anchor system of claim 6 wherein the anchor head further comprises:
   a reduced dimension neck region; and
   an outwardly tapered region positioned proximally from the neck region; wherein the socket in an unexpanded configuration is compatible with the neck and outwardly tapered regions, wherein the slits in the flange expand to fit the socket over the outwardly tapered region of the anchor head, and the slits return to an unexpanded configuration when the anchor head is seated in the socket.

8. The anchor system of claim 1 further comprising:
   a boss proximate the slit; and
   a yoke on the restrictor adapted to engage the boss and inhibit deformation of the slit.

9. The anchor system of claim 1 wherein the extension member defines a lumen providing percutaneous access to the anchor head when coupled to the anchor secured to the patient's vertebrae.

10. The anchor system of claim 1 wherein the one or more slits includes a major slit having a first portion extending from the distal end of the extension member, a hook portion angled relative to the first portion, a second portion angled relative to the hook portion, and a keyhole portion at a proximal terminus of the slit.

11. A method of installing a spinal fixation construct onto a patient's spine, the method comprising the steps of:
   making a first incision in the patient's skin proximate selected vertebrae of the patient;
   mounting first and second anchors to first and second vertebra, respectively, wherein each anchor has an anchor head;
   coupling first and second extension members to the anchor head of the first and second anchors, respectively, wherein the coupling includes, for each extension member, temporarily expanding a first portion of the extension member such that the first portion fits onto the anchor head, and then restricting the first portion of the extension member after the anchor head is seated within the first portion to inhibit subsequent expansion of the extension member while the extension member is coupled to the respective anchor;
   aligning a slot in the first extension member with a slot in the second extension member; and
   passing an element of the spinal fixation construct through a lumen in one of the extension members for engagement with the associated anchor.

12. The method of claim 11 wherein the mounting step further comprises:
  screwing a threaded shaft on the anchor into the respective vertebrae.

13. The method of claim 11 wherein the coupling step further comprises:
  temporarily expanding a slit in the first portion of the extension member to permit the first portion of the extension member to fit onto the associated anchor head.

14. The method of claim 13 wherein the restricting step further comprises:
  mating a boss proximate the slit with a yoke to thereby inhibit expansion of the slit.

15. The method of claim 11 wherein the passing step further comprises:
  passing a vertebral connecting element through the lumen of at least one extension member and through the slots of the first and second extension members to the first and second anchor heads; and
  passing a set screw through the lumen in each extension member to secure the vertebral connecting element to the associated anchor head.

16. The method of claim 11 wherein the extension members extend percutaneously from the patient when they are coupled to the anchor heads and the anchors are mounted to the respective vertebrae.

17. The method of claim 11 further comprising:
  making a second incision spaced from the first incision;
  wherein the first and second anchors are inserted through the first and second incisions, respectively.

18. A spinal fixation construct comprising:
  a plurality of anchors each having a head and being adapted to be secured to a patient's vertebrae;
  a plurality of extension members each adapted to be selectively coupled to one of the anchor heads and to provide access to the anchor when coupled thereto;
  an expansion arrangement on a distal portion of each extension member permitting the distal portion of the extension member to expand during installation and removal of the extension member on to and from, respectively, the associated anchor head, the expansion arrangement including a flange, a socket formed by the flange adapted to receive the anchor head, and at least one slit in the flange, wherein expansion of the slit allows the socket to expand to receive the anchor head, wherein the at least one slit includes a major slit having a first portion extending from a distal end of the extension member, a hook portion angled relative to the first portion, a second portion angled relative to the hook portion, and a keyhole portion at a proximal terminus of the slit;
  a plurality of restrictors each adapted to be selectively coupled to one of the extension members to inhibit expansion of the associated expansion arrangement when coupled thereto;
  a connecting member adapted to be coupled to selected anchors; and
  a plurality of fasteners each adapted to engage one of the anchor heads of the selected anchors and secure the connecting member relative to the selected anchor.

19. The spinal fixation construct of claim 18 wherein each extension member is elongate and adapted to extend percutaneously from the body when the associated anchor is secured to the patient's vertebrae.

20. The spinal fixation construct of claim 18 further comprising:
  a boss proximate each slit; and
  a yoke on each restrictor adapted to engage the boss and inhibit expansion of the slit.

21. The spinal fixation construct of claim 18 further comprising:
  a slot in a sidewall of selected extension members to provide access to an adjacent extension member and the associated anchor.

22. A vertebral anchor system comprising:
  an anchor having a head and being adapted to be secured to a patient's vertebrae;
  an extension member adapted to be selectively coupled to the anchor head to provide percutaneous access to the anchor when coupled thereto, the extension member having one or more major slits extending proximally from a distal end of the extension member, the major slit having a first portion and a second portion angled relative to the first portion, the extension member having one or more minor slits extending from the distal end of the extension member, wherein the major slit and minor slit are configured to expand when the extension member is inserted over the anchor head; and
  a first slot in a sidewall of the extension member adapted to provide access to regions of the spine adjacent to the anchor, wherein the first slot extends substantially the full height of the extension member, the extension member including a second slot in the sidewall extending less than the full height of the extension member.

* * * * *

UNITED STATES PATENT AND TRADEMARK OFFICE
CERTIFICATE OF CORRECTION

| | | |
|---|---|---|
| PATENT NO. | : 7,931,673 B2 | |
| APPLICATION NO. | : 11/567238 | |
| DATED | : April 26, 2011 | |
| INVENTOR(S) | : Hugh D. Hestad et al. | |

It is certified that error appears in the above-identified patent and that said Letters Patent is hereby corrected as shown below:

Column 6
Line 49, delete "go", and insert therefor -- 90 --.

Signed and Sealed this
Twenty-first Day of June, 2011

David J. Kappos
*Director of the United States Patent and Trademark Office*